(12) United States Patent
Kanaley et al.

(10) Patent No.: US 10,082,502 B2
(45) Date of Patent: Sep. 25, 2018

(54) CONTROLLING FLUID FLOW THROUGH AN ASSAY DEVICE

(71) Applicant: Ortho-Clinical Diagnostics, Inc., Raritan, NJ (US)

(72) Inventors: James D. Kanaley, Honeoye Falls, NY (US); Zhong Ding, Pittsford, NY (US); Philip C. Hosimer, Rochester, NY (US); Edward R. Scalice, Penfield, NY (US); Susan Danielson, Honeoye, NY (US); David A. Tomasso, Rochester, NY (US); Timothy C. Warren, Rochester, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 280 days.

(21) Appl. No.: 15/016,585

(22) Filed: Feb. 5, 2016

(65) Prior Publication Data

US 2016/0153982 A1 Jun. 2, 2016

Related U.S. Application Data

(63) Continuation of application No. 13/744,641, filed on Jan. 18, 2013, now abandoned.

(Continued)

(51) Int. Cl.
*G01N 33/558* (2006.01)
*B01L 3/00* (2006.01)
*G01N 33/543* (2006.01)

(52) U.S. Cl.
CPC ........ *G01N 33/558* (2013.01); *B01L 3/50273* (2013.01); *G01N 33/54366* (2013.01); *B01L 2400/0406* (2013.01); *B01L 2400/086* (2013.01)

(58) Field of Classification Search
CPC ............ B01L 2200/10; B01L 2400/08; B01L 2400/0406; G01N 33/533
See application file for complete search history.

(56) References Cited

U.S. PATENT DOCUMENTS

| 5,120,643 A | 6/1992 | Ching et al. |
| 5,559,041 A | 9/1996 | Kang et al. |

(Continued)

FOREIGN PATENT DOCUMENTS

| EP | 2135676 A1 | 12/2009 |
| JP | 2010-014709 | 1/2010 |

(Continued)

OTHER PUBLICATIONS

Japanese Office Action for JP 2013-007020; dated: Mar. 7, 2017; 4 pages.

(Continued)

*Primary Examiner* — Erik B Crawford
(74) *Attorney, Agent, or Firm* — K&L Gates LLP; Louis C. Cullman; Joseph Arand

(57) ABSTRACT

An assay device includes: a detection zone which includes a first set of projections which are capable of generating capillary flow. A wicking zone (WZ) has a capacity to receive liquid sample flowing from the detection zone and includes a second set of projections which are capable of generating capillary flow. The WZ is rectangular in shape and the longer side of the rectangle extends in the direction of flow to thereby reduce the pressure gradient in the assay device which increases the total flow time of liquid sample compared to a WZ having equal length sides and same volume. At least a portion of the second set of projections have at least one dimension selected from a diameter, a center-to-center spacing, or a gap between projections that is (Continued)

different from the first set of projections, and is selected to increase the total flow time of the sample.

8 Claims, 10 Drawing Sheets

Related U.S. Application Data

(60) Provisional application No. 61/588,772, filed on Jan. 20, 2012.

(56) References Cited

U.S. PATENT DOCUMENTS

| | | |
|---|---|---|
| 5,714,389 A | 2/1998 | Charlton et al. |
| 6,139,800 A | 10/2000 | Chandler |
| 6,228,660 B1 | 5/2001 | May et al. |
| 6,372,542 B1 | 4/2002 | Martin et al. |
| 6,733,682 B1 | 5/2004 | Björkman et al. |
| 6,811,736 B1 | 11/2004 | Ohman et al. |
| 6,884,370 B2 | 4/2005 | Öhman et al. |
| 7,416,700 B2 | 8/2008 | Buechler et al. |
| 8,398,936 B2 | 3/2013 | Horiuchi et al. |
| 8,895,293 B2 | 11/2014 | Kanaley et al. |
| 8,974,749 B2 | 3/2015 | Bergman et al. |
| 2006/0210445 A1 | 9/2006 | Osterfeld et al. ............ 422/100 |
| 2006/0239859 A1 | 10/2006 | Ohman et al. ............... 422/100 |
| 2006/0285996 A1 | 12/2006 | Ohman et al. |
| 2006/0289787 A1 | 12/2006 | Ohman et al. |
| 2007/0231883 A1 | 10/2007 | Lindstrom et al. |
| 2007/0266777 A1 | 11/2007 | Bergman et al. ............ 73/61.41 |
| 2009/0311805 A1 | 12/2009 | Bergman et al. |
| 2010/0041154 A1 | 2/2010 | Ohman et al. ................... 436/8 |
| 2013/0189672 A1 | 7/2013 | Ding |
| 2013/0189673 A1 | 7/2013 | Scalice et al. |
| 2014/0206098 A1 | 7/2014 | Hosimer et al. |

FOREIGN PATENT DOCUMENTS

| | | |
|---|---|---|
| JP | 2010-525319 | 7/2010 |
| WO | WO 2003103835 A1 | 12/2003 |
| WO | WO 2005089082 A3 | 11/2005 |
| WO | WO 2005118139 A1 | 12/2005 |
| WO | WO 2006137785 A1 | 12/2006 |
| WO | WO 2007149042 A1 | 12/2007 |
| WO | WO 2008-127191 A1 | 10/2008 |
| WO | WO 2008/127191 A1 | 10/2008 |
| WO | WO 2009/088021 A1 | 7/2009 |
| WO | WO 2011/045436 A1 | 4/2011 |
| WO | WO 2011/144652 A2 | 11/2011 |

OTHER PUBLICATIONS

U.S. Appl. No. 14/333,571, Danielson et al., Jul. 17, 2014.
Presentation entitled "Forecast Technology—A Versatile Platform for POC Testing" by Ib Mendel-Hartvig, presented at the Oak Ridge Conference—Frontiers in Clinical Diagnostics, Apr. 16, 2009, Baltimore, Maryland.
U.S. Appl. No. 61/588,738, filed Jan. 20, 2012; Title: Assay Device Having Multiple Reagent Cells; 39 pages.
U.S. Appl. No. 61/588,758, filed Jan. 20, 2012; Title: Low Volume Assay Device Having Increased Sensitivity; 38 pages.
U.S. Appl. No. 61/588,779, filed Jan. 20, 2012; Title: Assay Device Having Multiplexing; 45 pages.
U.S. Appl. No. 61/588,745, filed Jan. 20, 2012; Title: Assay Device Having Uniform Flow Around Corners; 37 pages.
U.S. Appl. No. 61/588,899, filed Jan. 20, 2012; Title: Assay Device Having Controllable Sample Size; 32 pages.
Japanese Office Action for JP 2013-007020; dated: Nov. 8, 2016; 4 pages.
Pretrial Reexamination Report for JP 2013-007020; dated: Aug. 15, 2017; 5 pages.

CONTROLLING FLUID FLOW THROUGH AN ASSAY DEVICE

CROSS REFERENCE TO RELATED APPLICATIONS

This patent application is a continuation of and claims priority benefit to U.S. Non-Provisional application Ser. No. 13/744,641, filed Jan. 18, 2013 and U.S. Provisional Application No. 61/588,772, filed Jan. 20, 2012, the disclosures of which are incorporated by reference in their entireties.

FIELD OF THE INVENTION

The present invention relates to the field of diagnostic assays, and in particular to lateral flow assays where an analyte to be detected is present in a biological or non-biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a reagent zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

A known non-porous assay device is shown in FIG. 1. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay). Unbound dissolved conjugate material will be swept past the detection zone into the at least one wicking zone 5. Also shown in FIG. 1 are projections or micropillars. An instrument such as that disclosed in US 20060289787A1, US20070231883A1, U.S. Pat. No. 7,416,700 and U.S. Pat. No. 6,139,800 all incorporated by reference in their entireties, are able to detect the bound conjugated material in the detection zone. Common labels include fluorescent dyes that can be detected by instruments which excite the fluorescent dyes and incorporate a detector capable of detecting the fluorescent dyes.

The sample size for such typical assay devices as shown in FIG. 1 are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "fingerstick" blood draw, which is on the order of 25 µl or less. Such a small amount of sample is the amount of blood in a drop of blood after pricking a finger tip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

To reduce the sample size required, the dimensions of the lateral flow assay devices are reduced to accommodate the smaller sample size. However, it has been found that reducing the sample size and dimensions of the device provides inadequate conjugate in the detection zone and accordingly less signal that can be read by the instrument, in some instances up to a 5× lower signal and poor sensitivity. The inadequate conjugate in the detection zone is believed to be due to reduced sample size and inefficient use of the sample in the device, amongst other conditions. Another drawback of reducing dimensions is the width of the detection zone will also be reduced, again making less signal available that can be read by the instrument. Also, it has been found that a smaller device has reduced flow time and conjugate material contact time, resulting in less binding between the analyte in the sample and the conjugate material. This is of particular concern for a smaller sample volume design described below. Throughout the remainder of the description the term "smaller sample volume" or "smaller volume" design is used interchangeably with "miniaturized" design.

Accordingly, there is a need for an assay device that can recover the loss of signal that occurs from reducing sample size in a smaller volume assay device. There is also a need for an assay device that can make more efficient use of sample in an assay device.

SUMMARY OF THE INVENTION

The present invention is directed to an assay device that alleviates one or more the foregoing problems described above.

One aspect of the invention is directed to an assay device, which includes: a liquid sample zone; a reagent zone downstream and in fluid communication with the sample zone containing a reagent material; a detection zone in fluid communication with the reagent zone, wherein the detection zone comprises a substrate and a first set of projections which extend substantially vertically from the substrate, wherein the projections have a height, cross-section and a distance between one another that defines a capillary space between the projections capable of generating capillary flow parallel to the substrate surface; and a wicking zone in fluid communication with the detection zone having a capacity to receive liquid sample flowing from the detection zone, wherein the wicking zone comprises a substrate and a second set of projections which extend substantially vertically from the substrate, wherein the projections have a height, cross-section and a distance between one another that defines a capillary space between the projections capable of generating capillary flow parallel to the substrate surface, wherein the wicking zone is rectangular in shape and the longer side of the rectangle extends in the direction of flow to thereby reduce the pressure gradient in the assay device which increases the total flow time of liquid sample compared to a wicking zone having equal length sides and same volume, and further wherein at least a portion of the second set of projections have at least one dimension selected from a diameter, a center-to-center spacing, or a gap between projections that is different from the first set of projections, and is selected to increase the total flow time of the sample through the device.

Another aspect of the invention is directed to an assay device that includes: a liquid sample addition zone; a reagent zone downstream and in fluid communication with the sample addition zone containing a reagent material; a detection zone in fluid communication with the reagent; and a wicking zone in fluid communication with the capture zone having a capacity to receive liquid sample flowing from the detection zone, wherein the wicking zone comprises a substrate and a second set of projections which extend substantially vertically from the substrate, wherein the projections have a height, cross-section and a distance between one another that defines a capillary space between the projections capable of generating capillary flow parallel to the substrate surface, and wherein the wicking zone is circular in shape which increases the pressure gradient in the assay device which decreases the total flow time of liquid sample compared to a square wicking zone having equal length sides.

Another aspect of the invention is directed to an assay device that includes: a liquid sample zone; a reagent zone downstream and in fluid communication with the sample zone containing a reagent material; a detection zone in fluid communication with the reagent zone; and a wicking zone in fluid communication with the detection zone having a capacity to receive liquid sample flowing from the detection zone, wherein the wicking zone comprises a substrate and projections which extend substantially vertically from the substrate, wherein the projections have a height, cross-section and a distance between one another that defines a capillary space between the projections capable of generating capillary flow parallel to the substrate surface, and wherein the wicking zone comprises barriers which provide a tortuous path for the fluid to follow, increasing the length of the flow path in the wicking zone which decreases the pressure gradient in the assay device which decreases the total flow time of liquid sample compared to an identically sized wicking zone having no barriers.

Another aspect of the invention is directed to an assay device comprising: a liquid sample zone; a reagent zone downstream and in fluid communication with the sample zone containing a reagent material; a detection zone in fluid communication with the reagent zone; and a wicking zone in fluid communication with the detection zone having a capacity to receive liquid sample flowing from the detection zone, wherein the wicking zone comprises a substrate and a set of projections which extend substantially vertically from the substrate, wherein the projections have a height, cross-section and a distance between one another that defines a capillary space between the projections capable of generating capillary flow parallel to the substrate surface, and wherein the projections are arranged in a row by row configuration and the gap between the rows of pillars is greater than the gap between pillars within a row.

Another aspect of the invention is directed to a method of controlling the flow rate of a sample through an assay device that that includes: providing a liquid sample zone; providing a reagent zone downstream and in fluid communication with the sample zone containing a reagent material; providing a detection zone in fluid communication with the reagent zone; providing a wicking zone in fluid communication with the detection zone having a capacity to receive liquid sample flowing from the detection zone, wherein the wicking zone comprises a substrate and projections which extend substantially vertically from the substrate, wherein the projections have a height, cross-section and a distance between one another that defines a capillary space between the projections capable of generating capillary flow parallel to the substrate surface, selecting the macroscopic dimensions of the wicking zone, wherein if a decreased total flow time of sample is desired, then the pressure gradient in the wicking zone is increased by at least one of decreasing the length of the flow path in the wicking zone relative to a square wicking zone with the same area and height (the same volume) and the same pillar arrangement, and if an increase in total flow time of sample is desired, then the pressure gradient in the wicking zone is decreased by at least one of increasing the length of the flow path relative to a square wicking zone with the same area and height (the same volume) and the same pillar arrangement or by increasing the pillar density at the flow channel prior to fluid entering the wicking zone.

Further objects, features and advantages of the present invention will be apparent to those skilled in the art from detailed consideration of the preferred embodiments that follow.

DETAILED DESCRIPTION OF PREFERRED EMBODIMENTS

Figure 1:
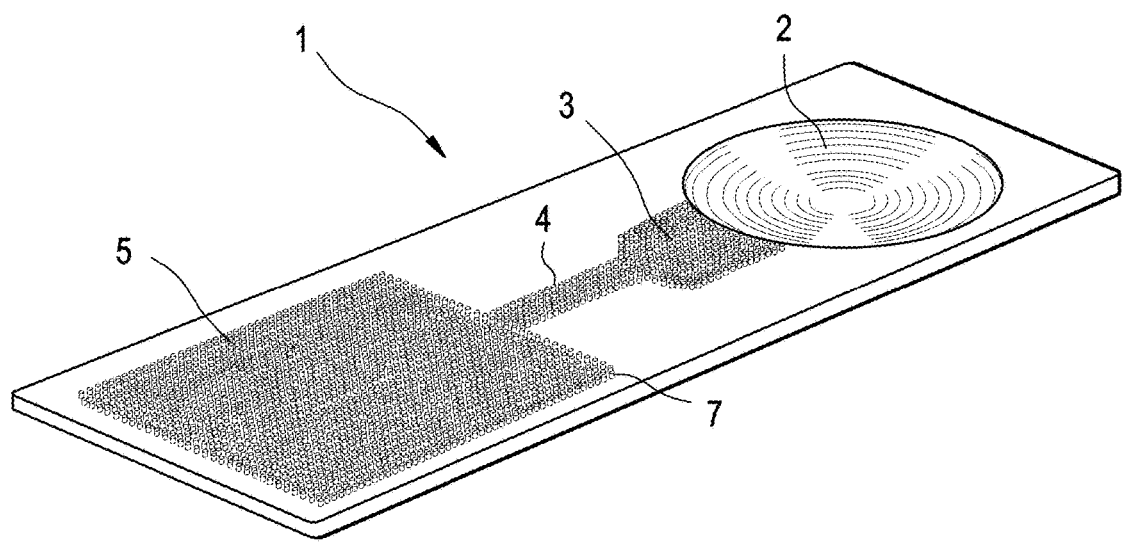
FIG. 1 shows a known assay device.

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

In the present invention, the determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" are used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

Figure 2:
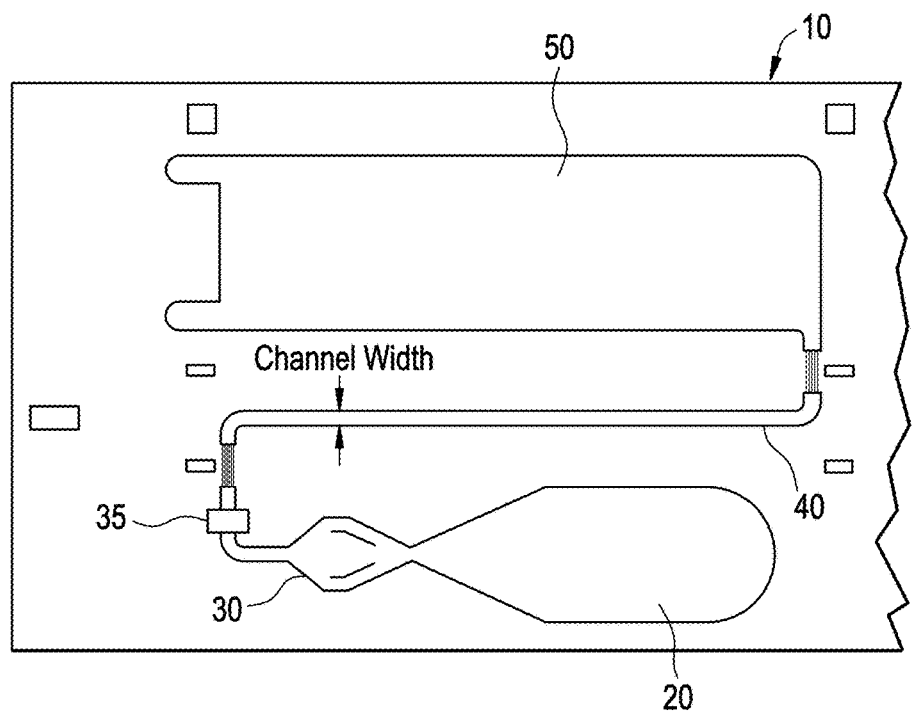
FIG. 2 shows a schematic view of an assay device according to one embodiment of the present invention.
Figure 3:
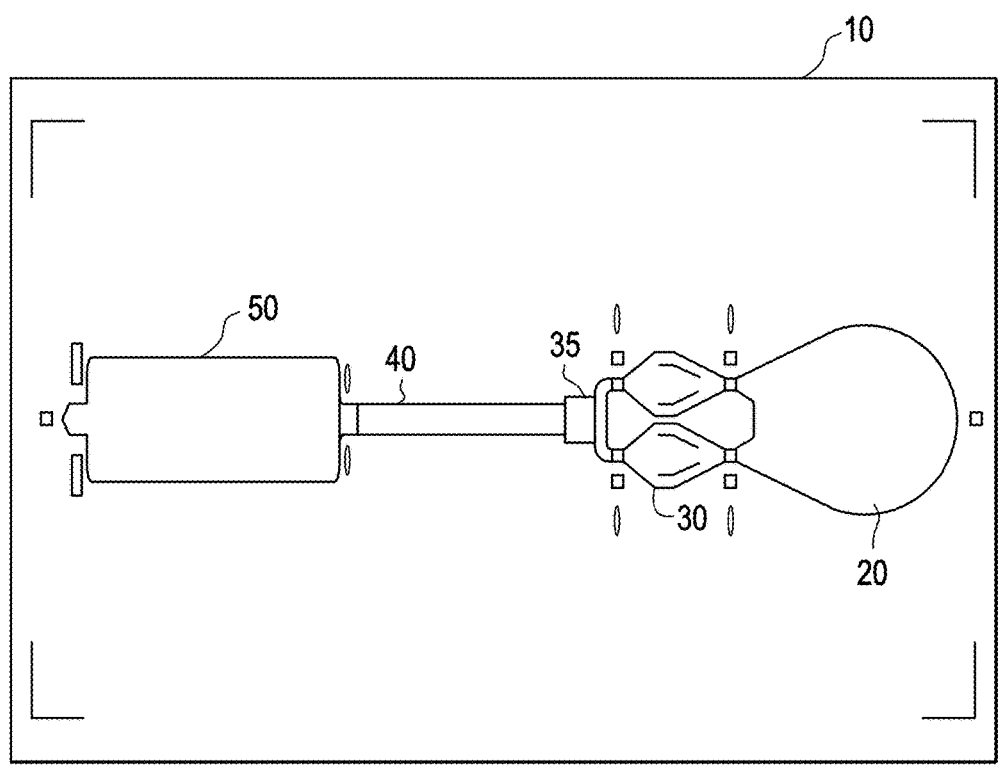
FIG. 3 shows a schematic view of an assay according to another embodiment of the invention.

The term "substrate" means the carrier or matrix to which a sample is added, and on or in which the determination is performed, or where the reaction between analyte and reagent takes place. The present invention is directed to a lateral flow assay device for determining the presence or amount of at least one analyte that solves, at least in part, the problem of lowered signal that can be detected due to the reduced sample size that is used in a miniaturized assay device. FIGS. 2 and 3 show schematic views of preferred embodiments of such devices according to the invention. The assay device 10, has at least one sample addition zone 20, at least one reagent zone 30, at least one detection zone 40, and at least one wicking zone 50. The zones form a flow path by which sample flows from the sample addition zone to the wicking zone. Also included are capture elements in the detection zone 40, capable of binding to the analyte, optionally deposited on the device (such as by coating); and a labeled reagent material also capable of binding to the analyte, located on the device in the reagent zone, wherein the labeled reagent material carries a first label for detection in the detection zone.

In order to achieve the desired goal of reducing the amount of sample required, the present inventors discovered that simply scaling down a conventionally sized device was insufficient because, as noted above, it resulted in insufficient signal being read by the instrument. Upon further investigation, it was discovered that in a conventionally sized assay device, i.e., one that uses on the order of 200 µl of blood, only about 10% of the analyte in the sample is captured and detected in the detection zone. While this may be a sufficient efficiency for larger sample sizes, such a low efficiency will result in insufficient signal for devices of the present invention that have significantly smaller dimensions and substantially less sample as compared to conventional devices.

In order to maximize analyte capture in a lower volume device and sample size, the present inventors found, after extensive research, that modifications were required in order to provide a miniaturized device having adequate signal. Briefly, these include:

Increasing the effective area of the detection zone by increasing the width of the dissolved reagent plume coming from the reagent zone and increasing the width of the flow path through the detection zone (described in co-pending application entitled "Lower Volume Assay Device Having Increased Sensitivity" (Application No. 61/588,758, first named inventor: Phil Hosimer) filed Jan. 20, 2012 and incorporated by reference in its entirety);

Increasing total assay flow time, to both increase the contact time between the reagent material and analyte in the reagent zone, and to increase contact time between analyte and the detection zone, which may include capture elements. These modifications are described in more detail below.

Components of the assay device (i.e., a physical structure of the device whether or not a discrete piece from other parts of the device) can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733, 682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 μm, preferably about 30 to about 100 μm, a diameter of about 10 to about 160 μm, preferably 30 to about 100 μm, and a gap or gaps between the projections of about 3 to about 200 μm, preferably 5 to 50 μm from each other. The flow channel may have a length of about 2 to about 100 mm, preferably about 5 to about 50 mm, and a width of about 0.1 to about 5 mm, preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 20, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 1. In those devices that can use finger stick volumes of blood, the sample can be directly touched off from the finger, or by a capillary pipette.

A filter material (not shown) can be placed in the sample addition zone to filter particulates from the sample or to filter blood cells from blood so that plasma can travel further through the device.

Located between the sample addition zone and the detection zone is a reagent zone 30. The reagent zone can include reagent(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. The amount of reagent in the reagent zone can be adjusted by the length of reagent deposited into the device while maintaining the same reagent width. The amount of reagent can also be adjusted by changing the width while maintaining the length. The amount of reagent can further be adjusted by changing both width and length simultaneously. In one preferred embodiment, the detection zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}$I and $^{32}$P.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 35 in FIGS. 2 and 3. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 35 is located after the reagent zone 30. According to a preferred embodiment, the reagent plume from the reagent zone should be as wide as possible to cover as much of the width of the detection zone as possible. One preferred embodiment for increasing the width of the reagent plume is described in co-pending application entitled "Assay Device Having Multiple Reagent Cells" (Application No. 61/588,738, first named inventor: Zhong Ding) filed Jan. 20, 2012 herewith and which is incorporated herein by reference in its entirety. In summary, multiple areas having reagent material (hereinafter referred to as "reagent cells") in a reagent zone along with elements to recombine multiple flow streams that result from the multiple reagent cells into one flow stream results in a more desirably mixed, wider reagent plume as it leaves the reagent zone and enters the detection zone.

Downstream from the liquid sample zone and the reagent zone is the detection zone 40 which is in fluid communication with the sample addition zone. The detection zone 40 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity" described above, are significantly narrower, e.g., 1.5 mm or less.

The detection zone is where any detectable signal is read. In a preferred embodiment attached to the projections in the detection zone are capture elements. The capture elements can include binding partners for the reagent or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent plume can include the conjugate having both the detection element and binding partner, in which case it is often referred to as a conjugate plume. As noted throughout, one challenge facing the inventors was to keep the reagent plume as wide as possible as it enters the detection zone.

As described above, one disadvantage of miniaturizing the assay device is a reduced total assay flow time which reduces the contact time for the reagent(s), sample, and any detection zone elements that may be present. The inventors have surprisingly found that total flow time can be increased by controlling the configuration of the wicking zone. Achieving longer flow time to the end of the wicking zone helps to increase the opportunity for analyte binding to intended moieties, increases signal and improves assay sensitivity.

More specifically, the inventors have found that the total assay flow time or flow rate of fluid through an assay device can be controlled by controlling the pressure gradient that is created by the capillary flow in the wicking zone. Reducing the pressure gradient across the length of the flow path in the direction of flow increases total flow time. Conversely, increasing the pressure gradient across the length of the flow path decreases total flow time.

The inventors have also found that an increased length of the flow path in the wicking zone compared to a square wicking zone having the same volume will result in a decrease of the pressure gradient, while a decreased length of the flow path will result in an increase of the pressure gradient, given the relationship $P_2-P_1$/Wicking Zone Length, where $P_2$ is the pressure at the end of the zone and $P_1$ is the pressure at the start of the zone.

One particularly preferred embodiment shown in FIGS. 2 and 3 uses a wicking zone 50 that is rectangular in shape and the longer side of the rectangle extends in the direction of flow. As noted above, the longer flow path created by the longer side of the rectangle, reduces the pressure gradient in the assay device which decreases the flow rate of liquid sample compared to a wicking zone having equal length sides.

Figure 4:
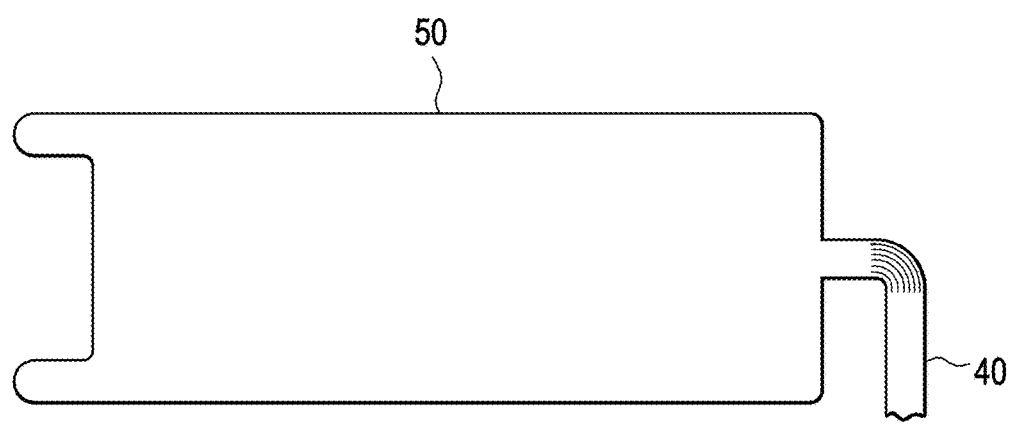
FIG. 4 shows a schematic view of a wicking zone having a center entrance according to an embodiment of the invention.

In a preferred embodiment, the fluid flow path from the detection zone will enter the wicking zone at the center of the shorter dimension of the wicking zone. It has been found that a side entry to the wicking zone such as shown in FIG. 2 may lead to filling of the wicking zone in a diagonal pattern, which may lead to trapped air bubbles. By having flow from the detection zone enter at the center point of the wicking zone, a more uniform flow may be achieved. A more uniform flow front is desirable for flow monitoring in the device. Entry at the center of the wicking zone is shown in FIGS. 3 and 4. The description of fluid flow through the device applies equally to the initial flow of liquid through the device (i.e., wetting) and well as steady state flow through the device after wetting.

The photographs show in FIGS. 9 and 10 illustrate the advantages of having flow enter the wicking zone at the center point. In FIGS. 9A-D the entrance 52 to the wicking zone is at the side of wicking zone 50. Fluid flow into the wicking zone is shown as the darker shading A. In FIG. 9B, the fluid is just starting to enter the wicking zone as shown in the top corner. As the fluid continues to enter the wicking zone, it does so in a manner that does not uniformly fill the wicking zone across the width (i.e., the wicking zones smaller dimension) and hence does not provide a uniform flow front. This may lead to trapped air and bubbles as noted above.

Figure 10A:
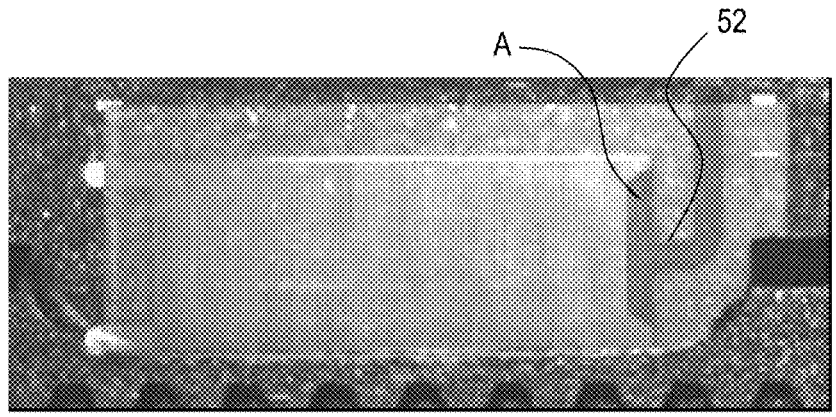
FIGS. 10A-C are photographs showing fluid entering the wicking zone from the center of the wicking zone according to a preferred embodiment of the present inventions.
Figure 10B:
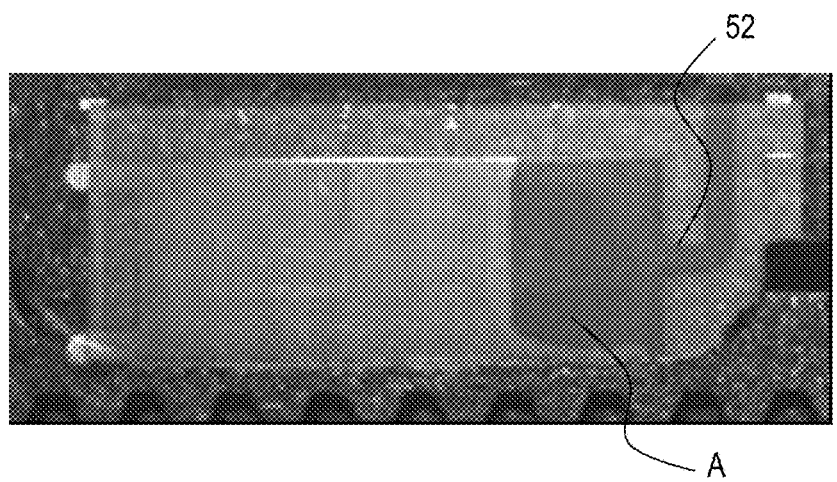
Figure 10C:
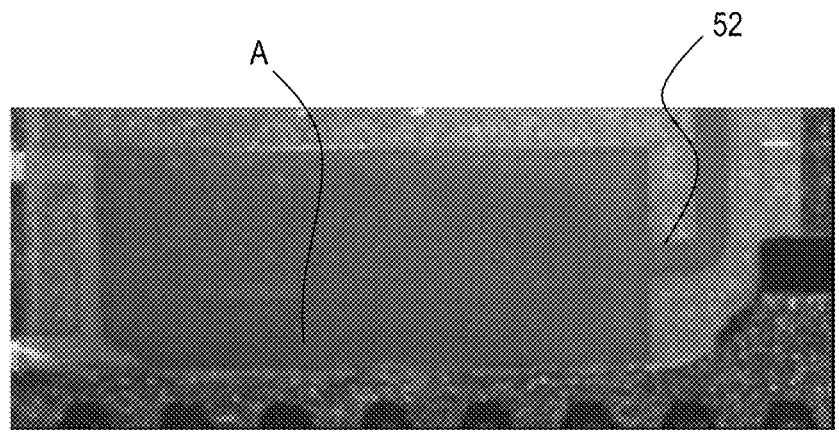

In contrast, FIGS. 10A-C depict the flow of fluid entering the wicking zone at the center point of the wicking zone. Again the fluid is shown as the darker shading A. In FIG. 10A, the fluid A is just beginning to enter the wicking zone from the right hand side. FIG. 10B shows the fluid filling about ⅓ of the wicking zone. As FIG. 10B shows, the fluid flow is uniform across the width of the wicking zone. FIG. 10C shows the filling of the wicking zone essentially complete. Again note the uniform flow of the fluid across the width of the wicking zone.

Figure 5:
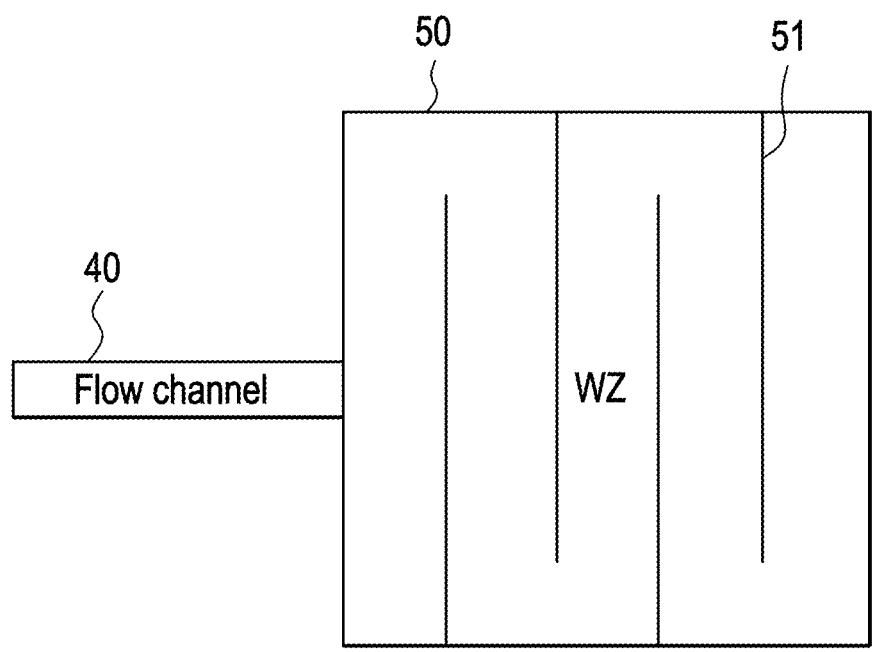
FIG. 5 shows a schematic view of a wicking zone having barriers according to an embodiment of the invention.

According to another embodiment of the invention, the length of the wicking zone flow path can be achieved by using structures such as internal barriers or walls within the wicking zone which will lengthen the flow path and slow the rate of fluid flow. The internal structures can be any structure that redirects flow in the wicking zone. They can be structures protruding from the substrate of the assay device and are formed in the same manner as the micro pillars described above. FIG. 5 depicts a wicking zone 50 having barriers 51 according to this embodiment of the invention.

Figure 6:
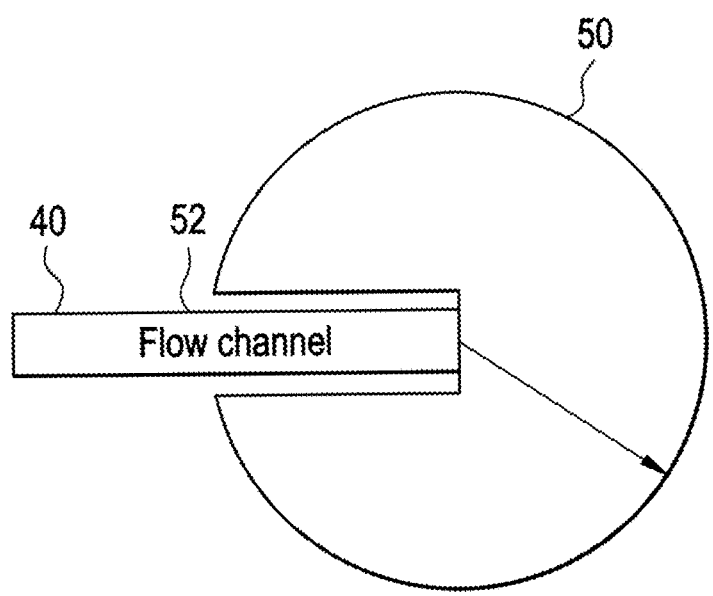
FIG. 6 shows a schematic view of a round wicking zone according to an embodiment of the invention.

To achieve a shorter total assay flow time, the wicking zone flow path can be decreased. FIG. 6 shows a circular wicking zone where the flow channel from the detection zone preferably delivers sample to the center of the wicking zone and the wicking zone flow path is equal to the radius of the circle. Barriers shown as 52 in FIG. 6 are present to ensure the fluid flow path from the detection zone enters the wicking zone at the center.

Figure 7:
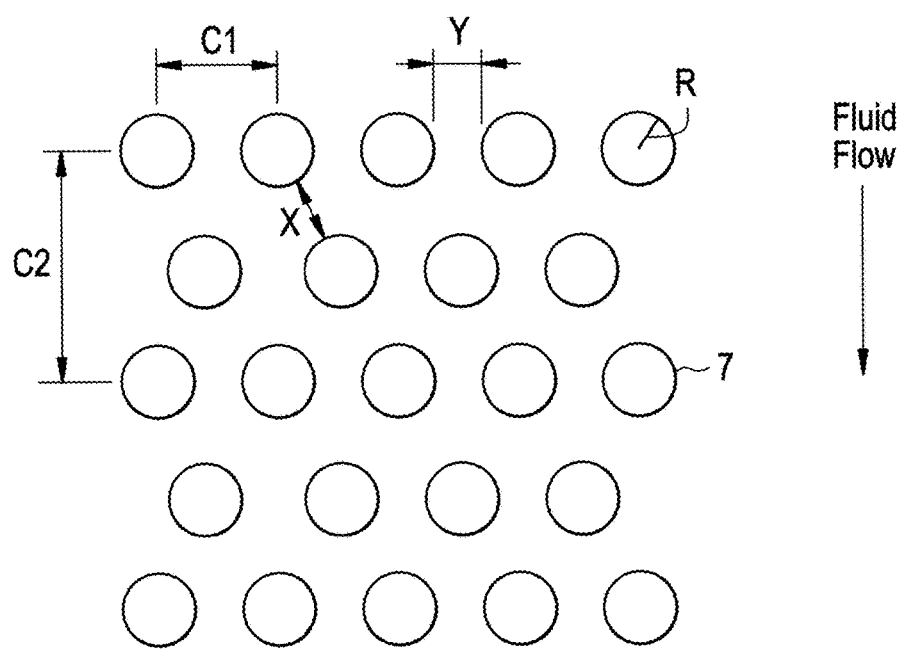
FIG. 7 shows the various dimensions that can affect pillar density and spacing.

In addition to controlling the flow time by changing the shape of the wicking zone, the inventors have also found that pillar density in the wicking zone plays a role in controlling the total flow time in an assay device. By increasing the pillar density the total flow time can be decreased, whereas decreasing density the total flow time can be increased. The dimensions that can be modified to control pillar density are shown in FIG. 7. FIG. 7 shows a top view of three rows of pillars used in the micropillar zone. The pillars have a radius R, a center-to-center spacing between pillars within a row of $C_1$, and a gap between the pillars within a row of Y. Gaps between pillars in adjacent rows in the flow direction are designated as X and the center-to-center spacing between pillars aligned in every other row as $C_2$. Varying any of these dimensions can affect the pillar density and hence the fluid flow rate of the assay device.

Decreasing or increasing the density of the projections or micro pillars to affect the total flow time does not have to be throughout the entire wicking zone. Instead, changing the density of the micro pillars near or at the entrance of the wicking zone will act as a rate limiting step for the fluid flow rate, since the fluid will first encounter the micro pillars as it enters the wicking zone from the detection zone.

Another aspect of controlling flow patterns includes decreasing pillar spacing ($C_1$ or Y) between pillars within a row and increasing the pillar spacing ($C_2$ or X) between rows in the flow direction to promote uniform flow patterns in the wicking zone. Images from flow computer simulations show that narrowing the pillar spacing for adjacent pillars within a row, and increasing the spacing between rows in the flow direction will retard the flow front from surging forward in the middle of the wicking zone and improve the overall uniformity of flow front. The tighter spacing within a row increases the capillary pressures or back pressures to hold the fluid front, and the larger distance between pillars in the flow direction reduces the relative pressure to proceed non-uniformly from row to row. In a preferred embodiment, the center-to-center spacing $C_1$ (as shown in FIG. 7) between adjacent pillars within a row is reduced in the range from 5% to 20%, and the spacing $C_2$ (as shown in FIG. 7) between every other row is increased in the range from 5% to 20%. In a particularly preferred embodiment, the center-to-center spacing $C_1$ between adjacent pillars within a row is reduced from 120 μm to 110 μm, and the spacing $C_2$ between every other row is increased from 286 μm to 312 μm.

Uniform row by row filling in the wicking zone enables accurate monitoring of the flow front in the wicking zone. This make is possible to engage in flow monitoring in the wicking zone for applications such as quality and process control, amongst others.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample zone of the assay device, such as through a port in the housing of the device, or by touching off a finger directly onto the sample addition zone in the case of a fingerstick blood draw. The sample moves by capillary action through an optional filter, and into the reagent zone where it dissolves the reagent material. In a preferred embodiment, the sample is reacted with a detection element in the case of a sandwich-type assay, either directly or indirectly, such as through an antibody. The sample flows away from the reagent zone having a dissolved reagent plume as it flows into the detection zone.

Next the sample moves by capillary action into the detection zone. In the detection zone, a signal representative of an analyte or control is produced. In a preferred embodiment the sample or the one or more reagents having a detection element is captured in the detection zone, such as by antibodies on the surface of the detection zone and a signal representative of the presence or concentration of the analyte(s) or control(s) is produced. The reader or detection instrument as described above is then used to read the signal that is produced in the detection zone to determine the presence or concentration of the analyte(s) or control(s). The sample moves from the detection zone and into the wicking zone. The reader may read the signal immediately or a short time after the sample has moved through the detection zone. Also, one or more washes may follow the sample through the device to wash any unbound reagents, such as detection element, away from the detection zone. As noted above, the wicking zone can be modified according to the present invention to control the flow of sample through the device.

Still another aspect of the invention is directed to a method of controlling the flow rate of a sample through an assay device. An assay device is provided that includes an liquid sample addition zone, the reagent zone and the wicking zone as described above. To control the flow rate of the sample, the macroscopic dimensions of the wicking zone is selected such that if a decreased total flow time of sample is desired, the pressure gradient in the wicking zone is increased by decreasing the length of the flow path in the wicking zone relative to a square wicking zone with the same area and height (the same volume) and the same pillar arrangement. If an increased total flow time of sample is desired, then the pressure gradient in the wicking zone is decreased by increasing the length of the flow path relative to a square wicking zone with the same area and height (the same volume) and the same pillar arrangement, and/or by increasing the pillar density at the area (or channel) prior to the entrance of the wicking zone without altering the pillar arrangement in the wicking zone.

The method, assay device, and reader according to an embodiment of the invention have many advantages, mainly related to the improved reaction kinetics of the immunochemical reactions and the increased sensitivity of the assay.

It is to be understood that this invention is not limited to the particular embodiments shown here. The following examples are provided for illustrative purposes and are not intended to limit the scope of the invention since the scope of the present invention is limited only by the appended claims and equivalents thereof.

Examples

Figure 8:
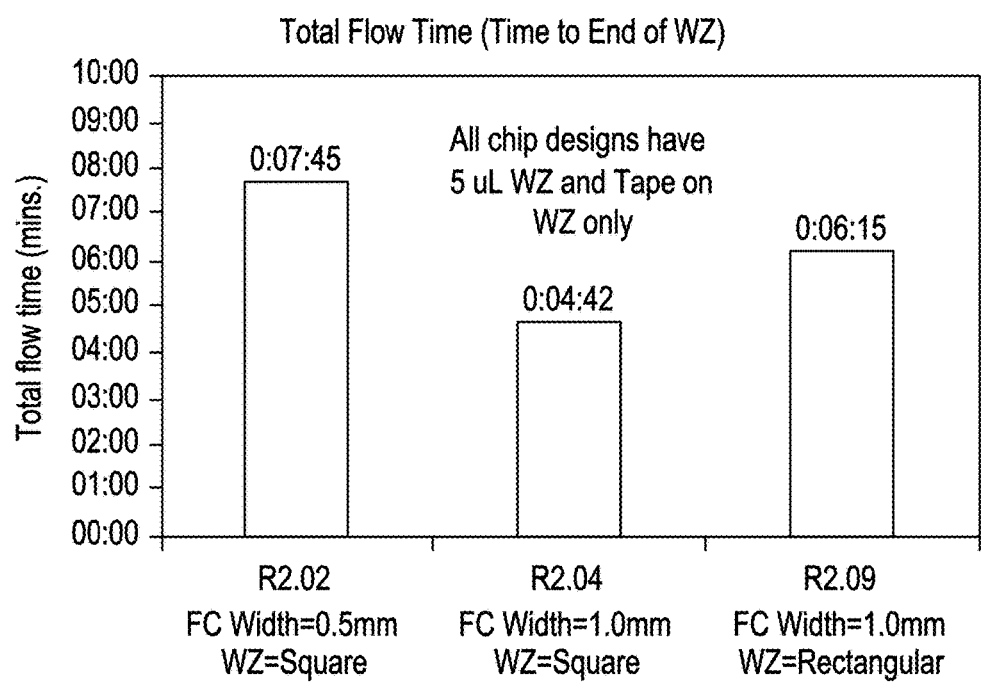
FIG. 8 shows the difference in total flow time for an assay device having a square wicking zone compared to an assay device having a rectangular wicking zone according to a preferred embodiment of the invention.
Figure 9A:
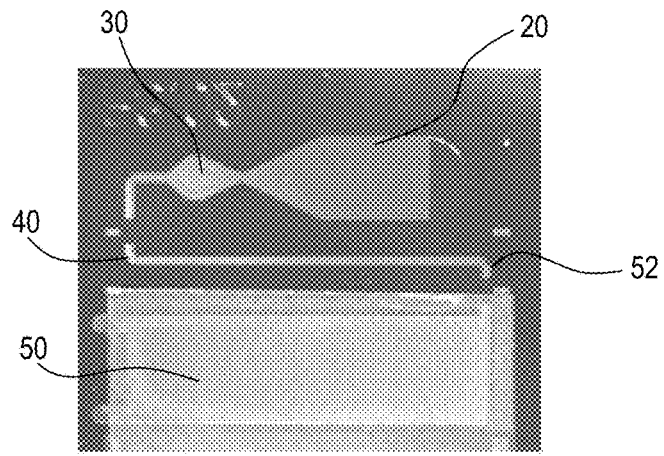
FIGS. 9A-D are photographs showing fluid entering the wicking zone from the side of the wicking zone.
Figure 9D:
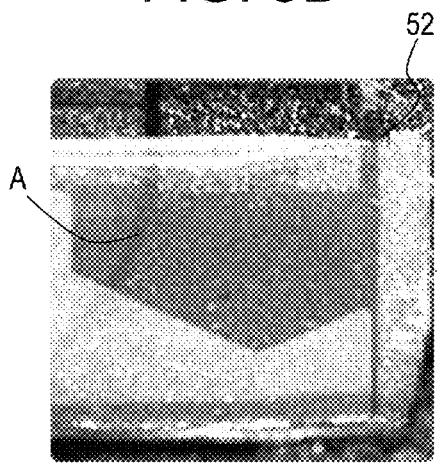
Figure 9C:
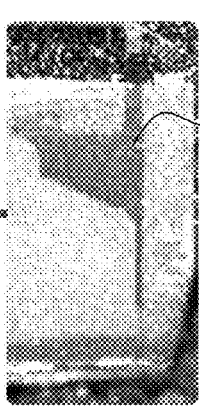
Figure 9B:
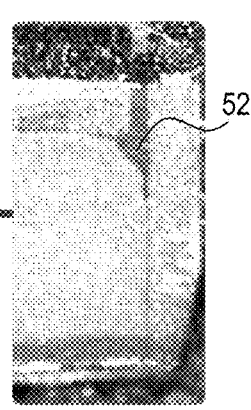

Plastic substrate chips made of Zeonor (Zeon, Japan) having oxidized dextran on the surface for covalently immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. The results are shown in FIG. 8 described below.

An assay device having wicking zone dimensions of (R2.04) 10 mm×10 mm and an assay device having wicking zone dimensions 4.5 mm and 22 mmm (R2.09) according to the present invention were prepared and tested for total flow time (i.e., the time it takes for the fluid flow front to reach the end of the wicking zone). In both devices, the wicking zone area is 100 mm2 and contains a fluid volume of 5 µL. Actual flow times are shown in the bar graph of FIG. 8, and indicate a 33% increase in flow time for R2.09 relative to the control R2.04. Also shown in comparison is an assay device (R2.02) having a detection zone flow channel width of 0.5 mm.

Additional Embodiments

1. An assay device comprising: a liquid sample zone; a reagent zone downstream and in fluid communication with the sample zone containing a reagent material; a detection zone in fluid communication with the reagent zone, wherein the detection zone comprises a substrate and a first set of projections which extend substantially vertically from the substrate, wherein the projections have a height, cross-section and a distance between one another that defines a capillary space between the projections capable of generating capillary flow parallel to the substrate surface; and a wicking zone in fluid communication with the detection zone having a capacity to receive liquid sample flowing from the detection zone, wherein the wicking zone comprises a substrate and a second set of projections which extend substantially vertically from the substrate, wherein the projections have a height, cross-section and a distance between one another that defines a capillary space between the projections capable of generating capillary flow parallel to the substrate surface, wherein the wicking zone is rectangular in shape and the longer side of the rectangle extends in the direction of flow to thereby reduce the pressure gradient in the assay device which increases the total flow time of liquid sample compared to a wicking zone having equal length sides and same volume, and further wherein at least a portion of the second set of projections have at least one dimension selected from a diameter, a center-to-center spacing, or a gap between projections that is different from the first set of projections, and is selected to increase the total flow time of the sample through the device.

2. An assay device as disclosed in embodiment 1, wherein the reagent material comprises a labeled reagent material, and the detection zone has capture elements bound thereto.

3. An assay device as disclosed in embodiment 1, wherein the longer/shorter side ratio of the wicking zone is greater than 1 and less than 10:1

4. An assay device as disclosed in embodiment 1, wherein the sample receiving zone, the reagent zone, the detection zone and the wicking zone define a fluid flow path.

5. An assay device as disclosed in embodiment 4, wherein the fluid flow path intersects the shorter side of the wicking zone at the midpoint thereof.

6. An assay device as disclosed in embodiment 1, wherein the portion of the second set of projections is located at the beginning of the wicking zone, where the sample and other materials enters the wicking zone.

7. An assay device as disclosed in embodiment 1, wherein the assay is a competitive assay.

8. An assay device as disclosed in embodiment 1, wherein at least a portion of the reagent material is bound to analyte in the liquid sample.

9. An assay device as disclosed in embodiment 8, wherein the assay is a sandwich-type assay.

10. An assay device comprising: a liquid sample addition zone; a reagent zone downstream and in fluid communication with the sample addition zone containing a reagent material; a detection zone in fluid communication with the reagent; and a wicking zone in fluid communication with the capture zone having a capacity to receive liquid sample flowing from the detection zone, wherein the wicking zone comprises a substrate and a second set of projections which extend substantially vertically from the substrate, wherein the projections have a height, cross-section and a distance between one another that defines a capillary space between the projections capable of generating capillary flow parallel to the substrate surface, and wherein the wicking zone is circular in shape which increases the pressure gradient in the assay device which decreases the total flow time of liquid sample compared to a square wicking zone having equal length sides.

11. An assay device as disclosed in embodiment 10, wherein the reagent material comprises a labeled reagent material, and the detection zone has capture elements bound thereto.

12. An assay device as disclosed in embodiment 10, wherein the sample receiving zone, the reagent zone, and the detection zone define a fluid flow path.

13. An assay device as disclosed in embodiment 12, wherein flow path directs the sample to the center of the wicking zone and the sample flows in all directions from the center.

14. An assay device as disclosed in embodiment 10, wherein the detection zone comprises a substrate and a first set of projections which extend substantially vertically from the substrate, wherein the projections have a height, cross-section and a distance between one another that defines a capillary space between the projections capable of generating capillary flow parallel to the substrate surface, and wherein further wherein at least a portion of the second set of projections have at least one dimension selected from a diameter, a center-to-center spacing, or a gap between projections that is different from the first set of projections, and is selected to decrease the total flow time of the sample through the device.

15. An assay device as disclosed in embodiment 1, wherein total area of the assay device is ≤900 mm$^2$.

16. An assay device as disclosed in embodiment 15, wherein total area of the assay device is ≤625 mm$^2$.

17. An assay device as disclosed in embodiment 1, wherein the assay device is square and the dimensions of each side are ≤30 mm.

18. An assay device as disclosed in embodiment 17, wherein the assay device is square and the dimensions of each side are ≤25 mm.

19. An assay device as disclosed in embodiment 1, wherein the assay device is capable of using a sample size of ≤30 μl.

20. An assay device as disclosed in embodiment 19, wherein the assay device is capable of using a sample size of ≤25 μl.

21. An assay device comprising: a liquid sample zone; a reagent zone downstream and in fluid communication with the sample zone containing a reagent material; a detection zone in fluid communication with the reagent zone; and a wicking zone in fluid communication with the detection zone having a capacity to receive liquid sample flowing from the detection zone, wherein the wicking zone comprises a substrate and projections which extend substantially vertically from the substrate, wherein the projections have a height, cross-section and a distance between one another that defines a capillary space between the projections capable of generating capillary flow parallel to the substrate surface, and wherein the wicking zone comprises barriers which provide a tortuous path for the fluid to follow, increasing the length of the flow path in the wicking zone which decreases the pressure gradient in the assay device which decreases the total flow time of liquid sample compared to an identically sized wicking zone having no barriers.

22. An assay device as disclosed in embodiment 21, wherein the reagent material comprises a labeled reagent material, and the detection zone has capture elements bound thereto.

23. An assay device comprising: a liquid sample zone; a reagent zone downstream and in fluid communication with the sample zone containing a reagent material; a detection zone in fluid communication with the reagent zone; and a wicking zone in fluid communication with the detection zone having a capacity to receive liquid sample flowing from the detection zone, wherein the wicking zone comprises a substrate and a set of projections which extend substantially vertically from the substrate, wherein the projections have a height, cross-section and a distance between one another that defines a capillary space between the projections capable of generating capillary flow parallel to the substrate surface, and wherein the projections are arranged in a row by row configuration and the gap between the rows of pillars is greater than the gap between pillars within a row.

24. An assay device as disclosed in embodiment 23, wherein the reagent material comprises a labeled reagent material, and the detection zone has capture elements bound thereto.

25. An assay device as disclosed in embodiment 1, wherein the fluid flow path intersects the wicking zone at the midpoint thereof.

26. An assay device as disclosed in embodiment 23, wherein the ratio of gap between the rows of pillars to the gap between pillars within a row is at least 2.5, more preferably >4.

27. A method of controlling the flow rate of a sample through an assay device that comprises: providing a liquid sample zone; providing a reagent zone downstream and in fluid communication with the sample zone containing a reagent material; providing a detection zone in fluid communication with the reagent zone; providing a wicking zone in fluid communication with the detection zone having a capacity to receive liquid sample flowing from the detection zone, wherein the wicking zone comprises a substrate and projections which extend substantially vertically from the substrate, wherein the projections have a height, cross-section and a distance between one another that defines a capillary space between the projections capable of generating capillary flow parallel to the substrate surface, selecting the macroscopic dimensions of the wicking zone, wherein if a decreased total flow time of sample is desired, then the pressure gradient in the wicking zone is increased by at least one of decreasing the length of the flow path in the wicking zone relative to a square wicking zone with the same area and height (the same volume) and the same pillar arrangement, and if an increase in total flow time of sample is desired, then the pressure gradient in the wicking zone is decreased by at least one of increasing the length of the flow path relative to a square wicking zone with the same area and height (the same volume) and the same pillar arrangement or by increasing the pillar density at the flow channel prior to fluid entering the wicking zone.

28. A method as disclosed in embodiment 27, wherein the reagent material comprises a labeled reagent material, and the detection zone has capture elements bound thereto.

29. A method as disclosed in embodiment 27, wherein the length of the flow path in the wicking zone is increased by providing barriers in the wicking zone to provide a tortuous path for the fluid to follow.

30. A method as disclosed in embodiment 27, wherein the length of the flow path in the wicking zone is increased by increasing the length of the wicking zone relative to the width.

31. A method as disclosed in embodiment 27, wherein the length of the flow path in the wicking zone is decreased by selecting a round wicking zone.

32. A method as disclosed in embodiment 27, wherein the flow path transports sample to the center of the wicking zone and the sample flows in all directions from the center.

Copending applications entitled "Low Volume Assay Device Having Increased Sensitivity" (Application No. 61/588,758, first named inventor: Phil Hosimer), "Assay Device Having Multiplexing" (Application No. 61/588,779, first named inventor: Sue Danielson), "Assay Device Having Multiple Reagent Cells" (Ser. No. 61/588,738, first named inventor Zhong Ding), "Assay Device Having Uniform Flow Around Corners" (Application No. 61/588,745, first named inventor James Kaneley), and "Assay Device Having Controllable Sample Size" (Application No. 61/588,899, first named inventor, Ed Scalice), all filed Jan. 20, 2012 and all incorporated by reference in their entireties.

What is claimed is:

1. An assay device comprising:
   a liquid sample zone;
   a reagent zone downstream and in fluid communication with the sample zone, the reagent zone containing a reagent material;
   a detection zone in fluid communication with the reagent zone, wherein the detection zone comprises a substrate and a first set of projections which extend substantially vertically from the substrate, wherein the first set of projections have a height, cross-section and a distance between one another that defines a capillary space between the projections capable of generating capillary flow parallel to the substrate surface; and
   a wicking zone adjacent to and in fluid communication with the detection zone having a capacity to receive liquid sample flowing from the detection zone,
   wherein the wicking zone comprises a substrate and a second set of projections which extend substantially vertically from the substrate, wherein the second set of projections have a height, cross-section and a distance between one another that defines a capillary space between the projections capable of generating capillary flow parallel to the substrate surface,
   wherein the wicking zone is rectangular in shape and the longer side of the rectangle extends in the direction of flow in order to reduce the pressure gradient in the assay device which increases the total flow time of liquid sample compared to a wicking zone having equal length sides and same volume, the wicking zone being defined by a beginning and an end, and
   further wherein at least a portion of the second set of projections at the beginning of the wicking zone have at least one dimension selected from a diameter, a center-to-center spacing, or a gap between projections that is different from the first set of projections, and is selected to reduce projection density as compared to the first set of projections and the remainder of the second set of projections, which increases the total flow time of the sample through the device, including the flow time of sample in the detection zone of the assay device.

2. The assay device as claimed in claim 1, wherein the reagent material comprises a labeled reagent material, and the detection zone has capture elements bound thereto.

3. The assay device as claimed in claim 1, wherein the longer:shorter side ratio of the wicking zone is greater than 1 and less than 10:1.

4. The assay device as claimed in claim 1, wherein the sample receiving zone, the reagent zone, the detection zone and the wicking zone define a fluid flow path.

5. The assay device as claimed in claim 4, wherein the fluid flow path intersects the shorter side of the wicking zone at the midpoint thereof.

6. The assay device as claimed in claim 1, wherein total area of the assay device is ≤900 mm$^2$.

7. The assay device as claimed in claim 4, wherein the fluid flow path intersects the wicking zone at the midpoint thereof.

8. The assay device as claimed in claim 1, in which the projections in the wicking zone are disposed in adjacent rows and in which the center to center spacing between adjacent projections in a row are narrowed as compared to the spacing between rows such that flowing sample is caused to fill a row before flowing to an adjacent row of projections.

* * * * *